US007481977B2

(12) United States Patent
Percival et al.

(10) Patent No.: US 7,481,977 B2
(45) Date of Patent: Jan. 27, 2009

(54) ASSAY DEVICE

(75) Inventors: David Alan Percival, Harwarden (GB); David Aubrey Plumptre, Droitwich (GB)

(73) Assignee: Bio-Rad Laboratories, Inc., Hercules, CA (US)

( * ) Notice: Subject to any disclaimer, the term of this patent is extended or adjusted under 35 U.S.C. 154(b) by 575 days.

(21) Appl. No.: 10/363,805

(22) PCT Filed: Sep. 6, 2001

(86) PCT No.: PCT/GB01/04005

§ 371 (c)(1), (2), (4) Date: Jul. 22, 2003

(87) PCT Pub. No.: WO02/20160

PCT Pub. Date: Mar. 14, 2002

(65) Prior Publication Data
US 2004/0038422 A1 Feb. 26, 2004

(30) Foreign Application Priority Data
Sep. 6, 2000 (GB) .................................. 00218875

(51) Int. Cl.
G01N 21/00 (2006.01)
G01N 35/00 (2006.01)
G01N 9/30 (2006.01)
B01D 33/00 (2006.01)
B04B 1/16 (2006.01)
B04B 5/02 (2006.01)

(52) U.S. Cl. ........................... 422/64; 436/45; 210/324; 494/4; 494/19; 422/72

(58) Field of Classification Search .................. 436/518, 436/165, 45; 422/64, 72; 210/324; 494/4, 494/19
See application file for complete search history.

(56) References Cited

U.S. PATENT DOCUMENTS

| 3,834,372 | A | 9/1974 | Turney |
| 4,507,977 | A | 4/1985 | Cabrera |
| 4,515,889 | A | 5/1985 | Klose et al. |
| 4,676,952 | A | 6/1987 | Edelmann et al. |
| 4,690,801 | A | 9/1987 | Anderson |
| 4,695,430 | A | 9/1987 | Coville et al. |
| 4,726,932 | A | 2/1988 | Feier et al. |
| 4,753,775 | A | 6/1988 | Ebersole et al. |
| 4,871,683 | A | 10/1989 | Harris et al. |
| 4,877,586 | A | 10/1989 | Devaney, Jr. et al. |

(Continued)

FOREIGN PATENT DOCUMENTS

AU 199914919 B2 7/1999

(Continued)

*Primary Examiner*—Jill Warden
*Assistant Examiner*—Lore Ramillano
(74) *Attorney, Agent, or Firm*—Townsend and Townsend and Crew LLP

(57) ABSTRACT

A device for fluid assay comprising a carousel (12), mounted about a hub (14), disposed in a complementary shaped housing (16). The carousel (12) is divided into a plurality of chambers (20, 22, 24, 26, 28, 30) disposed radially about the hub (14). The chambers (20, 22, 24, 26, 28, 30) are arranged into pairs which are disposed diametrically opposite one another and which communicate with each other via the hub (14).

17 Claims, 3 Drawing Sheets

U.S. PATENT DOCUMENTS

| Patent | Date | Inventor |
|---|---|---|
| 4,889,692 A | 12/1989 | Holtzman |
| 4,933,147 A | 6/1990 | Hollar et al. |
| 4,940,527 A | 7/1990 | Kazlauskas et al. |
| 4,981,801 A | 1/1991 | Suzuki et al. |
| 5,008,081 A | 4/1991 | Blau et al. |
| 5,073,029 A | 12/1991 | Eberly et al. |
| 5,160,702 A | 11/1992 | Kopf-Sill et al. |
| 5,186,844 A | 2/1993 | Burd et al. |
| 5,242,803 A * | 9/1993 | Burtis et al. ................ 435/7.92 |
| 5,270,212 A | 12/1993 | Horiuchi et al. |
| 5,402,240 A | 3/1995 | Thistlethwaite et al. |
| 5,457,053 A * | 10/1995 | Burd et al. .................... 436/45 |
| 5,478,750 A | 12/1995 | Bernstein et al. |
| 5,482,626 A | 1/1996 | Lohnes et al. |
| 5,496,520 A * | 3/1996 | Kelton et al. .................. 422/64 |
| 5,507,410 A | 4/1996 | Clark et al. |
| 5,573,951 A | 11/1996 | Gombrich et al. |
| 5,580,524 A | 12/1996 | Forrest et al. |
| 5,585,068 A | 12/1996 | Panetz et al. |
| 5,591,643 A | 1/1997 | Schembri |
| 5,627,041 A | 5/1997 | Shartle |
| 5,630,986 A | 5/1997 | Charlton et al. |
| 5,660,727 A | 8/1997 | Gleave et al. |
| 5,695,949 A | 12/1997 | Galen et al. |
| 5,863,506 A | 1/1999 | Farren |
| 5,885,529 A | 3/1999 | Babson et al. |
| 5,935,858 A | 8/1999 | Herbst |
| 6,027,692 A | 2/2000 | Galen et al. |
| 6,096,276 A | 8/2000 | Laursen |
| 6,241,689 B1 | 6/2001 | Chard et al. |
| 6,300,142 B1 * | 10/2001 | Andrewes et al. ........... 436/518 |

FOREIGN PATENT DOCUMENTS

| | | |
|---|---|---|
| WO | WO 99/28038 | 6/1999 |

* cited by examiner

ASSAY DEVICE

The present invention relates to an assay device, apparatus and method for use in fluid assays. In particular it relates to a device for use in body fluid assays, for example assays on blood and urine. More particularly, it relates to a device for use in assays for glaciated proteins in body fluid samples.

PCT/GB98/03586 discloses an apparatus for conducting an assay comprising a first inlet, a second inlet, and an inlet port, the inlet port being moveable relative to each of said first and second inlets such that the port can be brought into liquid communication with each inlet in turn as required, the inlet port accommodating a filter means and/or a binding retaining means.

In the course of conducting an assay, for example, to determine the presence or absence of one or more analyses in a sample, the sample is separated into first component fraction and a second component fraction, the second component fraction being obtained by eluting a compound "held" on the binder retaining means from the binder retaining means.

It is an aim of the present invention to provide a device, apparatus and method for automated fluid assay which is simpler for the end user and is less prone to user error.

In accordance with the first aspect of the present invention there is provided a device for fluid assay comprising a carousel mounted on a hub having an assay component separation zone, the carousel being rotatable about the hub to provide multiple configurations of the device, the carousel having a plurality of chambers being non-communicating in a first configuration of the device, a first chamber communicating through the separation zone with at least one other chamber in a second configuration of the device.

Preferably the device further comprises a second chamber which communicates through the separation zone with at least one other chamber in a third configuration of the device.

More preferably, the device further comprises a third chamber which communicates through the separation zone with at least one other chamber in a fourth configuration of the device.

In addition to being rotatably about the hub, the carousel may be rotatable with the hub. This facilitates thorough contacting of the contents of the chambers.

Preferably, the device is cooperable with drive means for automated fluid assay.

The device may be keyed so it may only fit in one orientation within an apparatus.

Preferably the fluid for assay is a body fluid, which includes blood, blood components, such as serum or plasma, and urine.

Preferably the separation zone comprises a transverse channel in the hub. More preferably the channel is inclined with respect to the longitudinal axis of the hub.

The separation zone is preferably a chromatographic separation zone. The zone may be at least partially blocked by a filter material or binding retaining material effective for chromatographic separation. Preferably the zone is completely blocked by a filter material or binding retaining material effective for chromatographic separation.

The filter material or binding retaining material is preferably a frit.

Preferably the chambers are disposed radially about the hub. More preferably communicating chambers are disposed diametrically opposite one another about the hub.

Preferably the device comprises an openable port disposed in the first chamber for charging a fluid to be assayed.

Preferably at least one chamber comprises walls which comprise material effective for allowing the passage of light therethrough.

The carousel and hub may be manufactured from the same or different material. Preferably they are manufactured from different materials.

The carousel and hub are preferably manufactured from plastics.

The carousel may be manufactured from acrylic material. The hub may be manufactured from polystyrene or acrylic material. Preferably, the hub or carousel comprise a plastics coating. More preferably, the hub or carousel comprises a thermo-polyethylene coating. More preferably still the hub or carousel comprises a santoprene (RTM) coating.

Manufacturing the hub and carousel from different materials facilitates the liquid sealant properties therebetween. It precludes the use of grease or other such sealants which would interfere with the accuracy of the assay.

The central hub may have a diameter in the range of 8 to 18 mm. Preferably the hub has a diameter in the range between 10 to 15 mm. More preferably still, the hub has a diameter of 13 mm.

Preferably the device comprises means for venting. More preferably means for venting comprises venting apertures in the device. More preferably still, the venting apertures are releasably sealed by foil before use of the device.

The device may comprise means for bursting foil sealed apertures. The means for bursting foil sealed apertures may comprise at least one spike, barb or the like. Preferably, the means comprise a plurality of spiles.

The device may comprise 'teeth' for co-operating with a drive means for automated fluid assay.

In accordance with a second aspect of the present invention there is provided an apparatus for fluid assay comprising means for vertically mounting a device as described hereinabove whereby the flow of fluid through the separation zone in the second configuration is facilitated by gravity.

The instrument may comprise means for bursting foil sealed venting apertures in the device or may comprise means for engaging with means for bursting foil sealed venting apertures dispoed on the device.

The instrument may comprise a cog drive to co-operate with teeth disposed on the device for automated fluid assay.

In accordance with a third aspect of the present invention there is provided a method for fluid assay comprising the use of a device or apparatus as described hereinabove, comprising the steps of:

(a) contacting a fluid to be assayed in the first chamber with an assaying reagent in the first configuration of the device;
(b) rotating the carousel to the second configuration of the device;
(c) collecting a component to be assayed in at least one other chamber;
(d) assaying the component.

Specific embodiments of the present invention will now be described with reference to the figures by way of example only:

FIG. 4 comprises said means.

Figure 1:
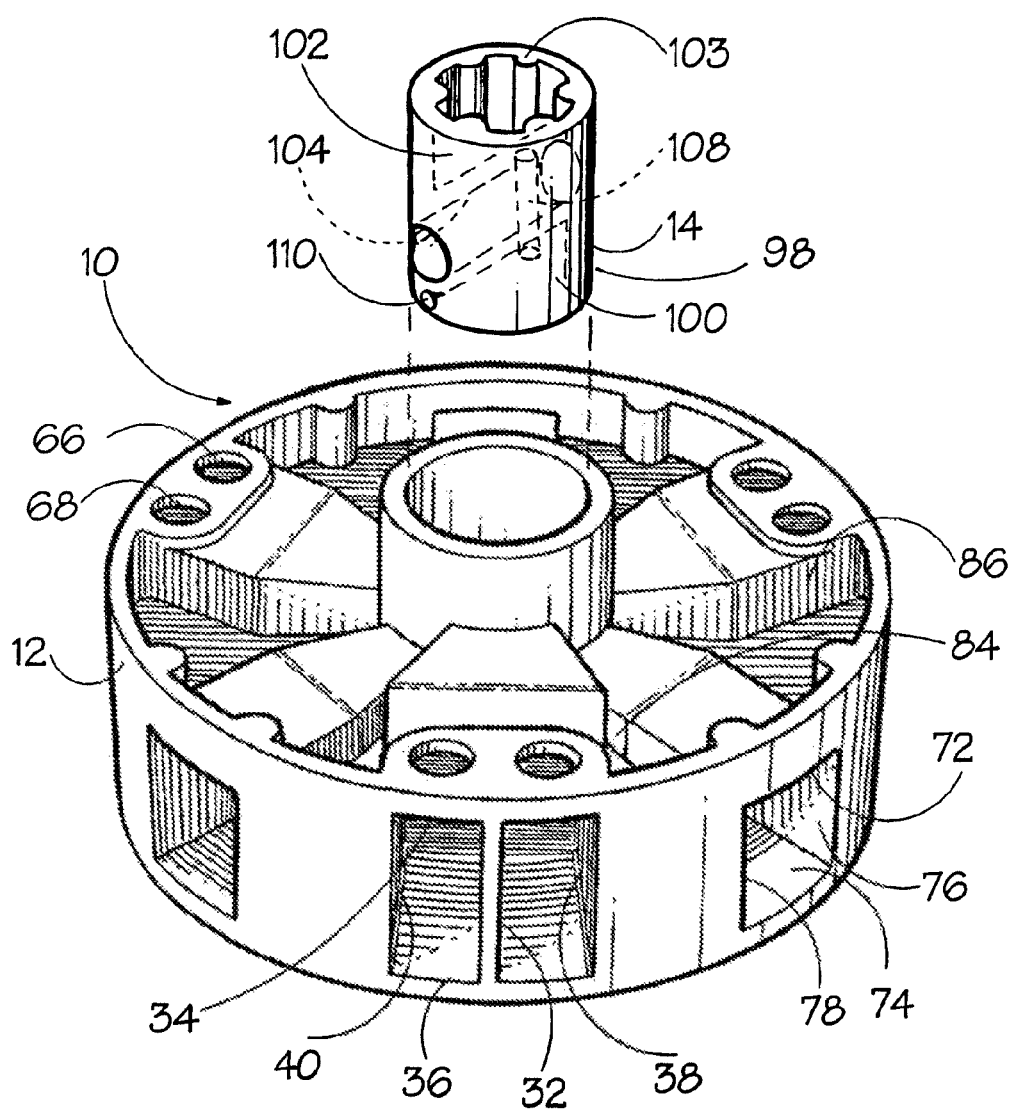
FIG. 1 is a perspective view of a device according to one aspect of the invention.
Figure 2:
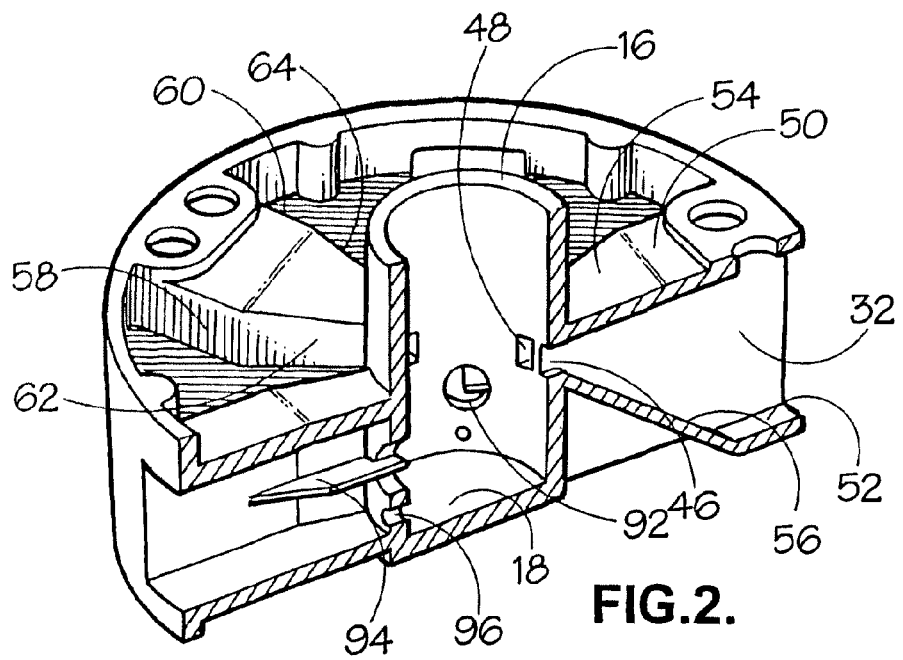
FIG. 2 is a partial sectional view of the FIG. 1 device.
Figure 3:
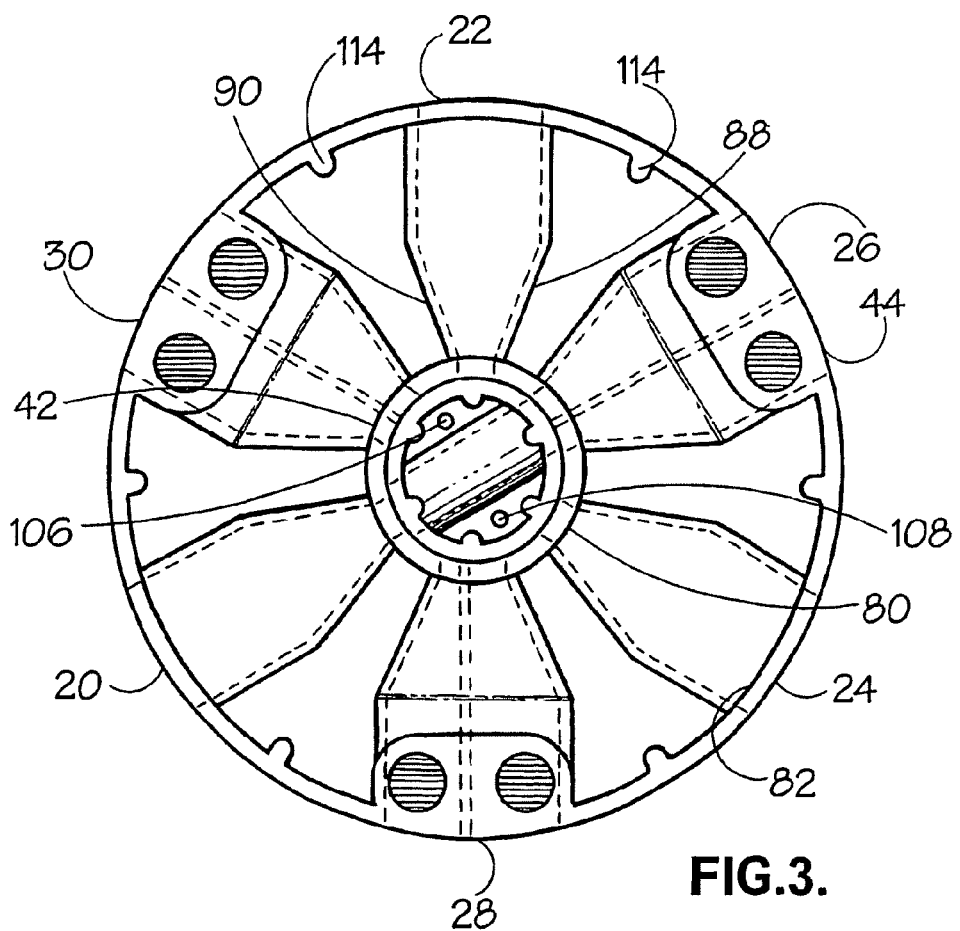
FIG. 3 is a plan view of the FIG. 1 device.

The device 10 comprises a carousel 12 rotatably mounted about a hub 14, disposed in a complementary shaped housing 16 having a lower end wall 18.

The carousel is divided into a plurality of chambers. There are three optical chambers 20, 22, 24 and three reagent chambers 26, 28, 30. The six chambers are radially disposed about the hub 14 and are arranged into pairs which are disposed diametrically opposite one another. Each pair comprises a reagent chamber and an optical chamber. In the case of an assay for determining glaciated and non-glaciated proteins in hemoglobin the reagent chambers 26, 28, 30 contain respectively, a) a buffer and an amino phenyl boronate agarose (aPBA) matrix;
b) a wash buffer; and
c) an eluting buffer.

Each reagent chamber 26, 28, 30 has centrally disposed dividing wall 32 running along its longitudinal axis. Each reagent chamber has an upper and lower wall 34 36, two side walls 38 ,40 an inner end wall 42 proximally disposed with respect to the carousel and an outer end wall 44 distally disposed with respect to the carousel.

Inner end wall 42 has two apertures 46, 48 adjacently disposed to upper wall 34 and either side of the dividing wall 32.

Upper and lower walls 34, 36 each have a parallel face 50, 52 with respect to one another and an inclined face 54, 56 which converge on apertures 46, 48.

Side walls 38 ,40 each have a parallel face 58, 60 with respect to one another and an inclined face 62, 64 which converge on apertures 46, 48.

Upper wall 34 further comprises a pair of apertures 66,68 disposed either side of dividing wall 32 adjacent to outer end wall 44. Each aperture 66,68 is sealed temporarily by foil, one of which serves as a vent when the device is in use with the exception of one aperture disposed in the first reagent chamber 26 which has a resealable cap facilitating the introduction of a sample (not illustrated).

Optical chambers 20, 22, 24 have upper and lower walls 72,74 parallel with respect to one another, two side walls 76,78 and an inner end wall 80 proximally disposed with respect to the carousel and an outer end wall 82 distally disposed with respect to the carousel.

Side walls 76,78 each have a parallel face 84,86 with respect to one another and an inclined face 88,90 convergent on inner end wall 80.

Centrally disposed in inner end wall 80 is an aperture 92 which communicates with a channel 104 disposed in hub 14 described hereinbelow variously as channel or tube 104.

Extending perpendicularly from the inner face of side wall 76 and centrally disposed is drip catcher 94 which serves to ensure that all of the sample which passes through the channel in hub 14 is collected in the optical chamber.

Optical chambers 20, 22, 24 further comprise a venting aperture 96 in inner end wall 80 adjacently disposed to lower wall 74 which communicates with a venting in hub 14 described hereinbelow.

Each chamber pair is brought into liquid communication via the channel 104 disposed in hub 14.

Hub 14 comprises a cylinder 98 divided into two compartments 100,102 by an inclined transverse channel or tube 104. Compartments 100,102 communicate via venting apertures 106,108 disposed either side of channel or tube 104. Compartment 100 communicates with each of the optical chambers 20, 22, 24 via a venting aperture 110 in the cylinder wall complementary in shape with venting aperture 92. Channel/tube 104 is blocked at one end, adjacent to aperture 110, by a frit (not illustrated). Compartment 102 has a plurality of projections 112 extending from the inner wall of the cylinder which serve to engage with a drive means when the device is used in automated fluid assay. Carousel 12 also has a plurality of projections 114 which serve to engage with a drive means when the device is used in automated fluid assay. When carousel 12 is mounted about hub 14, a volume defined by cylinder 98 constitutes an assay component separation zone. In configurations described below which result from rotation of carousel 12 about hub 14, an assay component in a chamber is either prevented from communicating with another chamber by cylinder 98 or is allowed to communicate with the other chamber across the assay component separation zone through channel/tube 104 of cylinder 98.

In use the device 10 is mounted vertically in apparatus comprising drive means. A sample, for example blood, is loaded in the first reagent chamber 26 via the aperture 66 in the first reagent chamber whilst in the first configuration. Once aperture 66 has been resealed with cap the device is rotated through 360° to ensure thorough mixing, and in this example to facilitate lysing of the red blood cells thereby liberating the hemoglobin. The device is left for 60-90 seconds during which the glaciated hemoglobin present in the sample binds to the aPBA affinity matrix.

Once mixed the carousel 12 is held in place such that the first reagent chamber 26 is disposed above the first optical chamber 20 and the hub 14 is rotated such that reagent chamber 26 communicates with optical chamber 20 via tube 98 in the second configuration of the device. At the same time the foil covering the venting aperture is punctured to permit venting, breaking the air lock, whilst at the same time venting is facilitated in the optical chamber via venting apertures 96, 106, 108, 110 causing the release of the reagent chamber's contents through the frit into the optical chamber below under the influence of gravity. The aPBA affinity matrix, however, is too large to pass through the frit and is retained in tube 104.

The reagent chamber's contents collect in the first optical chamber which contains the non-glaciated hemoglobin present in the original sample. The aPBA affinity matrix collected in tube 104 contains the glaciated hemoglobin present in the original sample.

The hub is then held in place and the carousel is rotated a further 60° such that the second reagent chamber 28 is brought into liquid communication with the second optical chamber 22 in the third configuration of the device, thereby presenting a wash for use and release of the reagent chamber's contents is facilitated as described for the second configuration. This step is to remove any non-specifically bound non-glaciated hemoglobin from the aPBA affinity matrix that may be present.

On rotating the carousel to a further 60° the third reagent chamber 30, containing the eluting solution is presented, in a fourth configuration of the device and release of the reagent chamber's contents. The elution buffer removes the glaciated hemoglobin from the aPBA affinity matrix which is collected in the optical chamber.

The apparatus spectrophotometrically measures the absorbance of both the non-glaciated and the glaciated hemoglobin fractions, and calculates the % glaciated hemoglobin present in the original whole blood sample.

Figure 4:
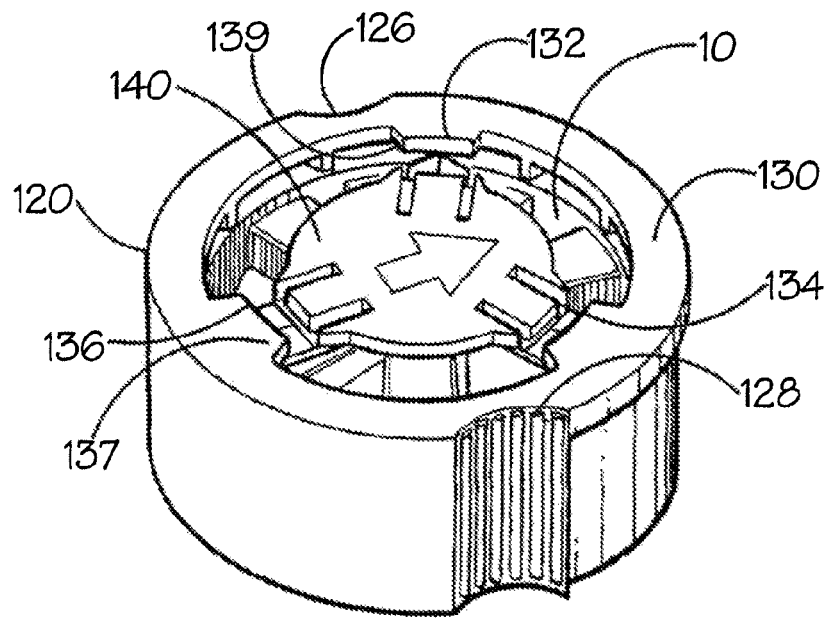
FIG. 4 is a perspective view from below of a further embodiment of the present invention.
Figure 5:
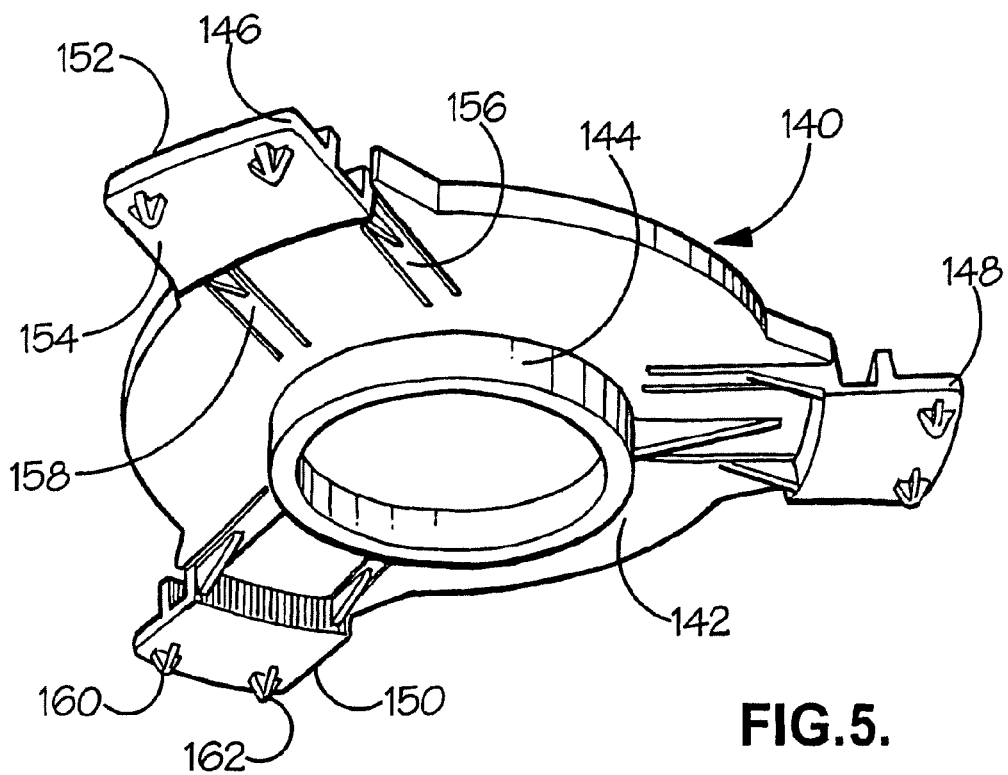
FIG. 5 is a perspective view from below of a foil piercing means.

In a further embodiment of the present invention, FIG. 4, a cylindrical sleeve 120, in which device 10 is disposed, has two recesses 126, 128 extending longitudinally and diametrically disposed from one another and having a knurled surface to facilitate handling.

First open end 122 is flush with the lower edge of carousel 12 (not illustrated) whilst second open end 124 has an inwardly extending lip 130, which engages the upper edge of carousel 12, and further has three inwardly extending tongues 132, 134, 136, having an upper and lower surface 137, 139, disposed equidistantly around lip 130 and adjacent to reagent chambers 26, 28, 30.

Disposed on housing 16 is a foil piercing means 140. Foil piercing means 140 has a substantially circular planar body 142 having a centrally disposed upstanding circular wall 144 dimensioned such that it accommodates housing 16. Body 142 has three radially extending tongues 146, 148, 150, disposed equidistantly and adjacent to reagent chamber 26, 28, 30, having upper and lower surfaces 152, 154. Each tongue 144, 146, 148 is fixed to body 142 via two sprung arms 156, 158. Disposed on the lower surface 154 of each tongue 144, 146, 148 are two spikes 160, 162. Spikes 160, 162 are shaped and spaced apart such that they overlie apertures 66, 68.

The upper surface 152 of each tongue 144, 146, 148 engages with the inner surface 137 of tongues 132, 134, 136.

In order to accommodate foil piercing means 140 and hub 14, end wall 18 of housing 16 is absent in the further embodiment, to permit drive means to engage with the hub. In the further embodiment compartment 100 has a plurality of projections extending from the inner wall (not illustrated).

In use the protocol is as set out hereinabove, with the exception that venting of apertures 66, 68 is facilitated as follows:—A ram located on the apparatus sequentially engages with tongues 144, 146, 148. Since tongues 144, 146, 148 are fixed via sprung arms, the tongues 144, 146, 148 are displaced such that spikes 160, 162 pierce the foil overlying apertures 66, 68, thereby facilitating venting.

Whilst the invention has been described with reference to an assay for determining the % levels of glaciated hemoglobin, the skilled man will appreciate that the number of reagent and optical chambers and the assay liquids will vary for other assay systems.

The invention claimed is:

1. A device for fluid assay comprising a carousel mounted on a hub comprising an assay component separation zone having a transverse channel formed therethrough and dividing the hub into two compartments, the carousel being rotatable about the hub to provide multiple configurations of the device, the carousel having a plurality of chambers being non-communicating across the assay separation zone in a first configuration of the device, a first chamber in fluid communication through the transverse channel of the separation zone with at least one other chamber in a second configuration of the device, and wherein a second chamber is in fluid communication through the transverse channel of the separation zone with at least one other chamber in a third configuration.

2. A device as claimed in claim 1, wherein a third chamber is in fluid communication through the transverse channel of the separation zone with at least one other chamber in a fourth configuration of the device.

3. A device as claimed in claim 1 wherein the device includes projections to engage with drive means of an automated fluid assay apparatus.

4. A device as claimed in claim 1 wherein the fluid is a body fluid which includes blood, blood components and urine.

5. A device as claimed in claim 1 wherein the separation zone is a chromatographic separation zone.

6. A device as claimed in claim 5, wherein the transverse channel is at least partially blocked by a filter material or binding retaining material effective for chromatographic separation.

7. A device as claimed in claim 6, wherein the filter means or binding retaining means is a frit.

8. A device as claimed in claim 1 wherein the chambers are disposed radially about the hub.

9. A device as claimed in claim 8, wherein said communicating chambers are disposed diametrically opposite one another about the hub.

10. A device as claimed in claim 1 further comprising an openable port disposed in the first chamber.

11. A device as claimed in claim 1 wherein at least one chamber is or comprises an optical material effective for allowing the passage of light therethrough.

12. A device as claimed in claim 1 wherein the carousel and hub are manufactured from different materials.

13. A device as claimed in claim 1 wherein at least one chamber comprises at least one aperture releasably and resealably sealed.

14. A device as claimed in claim 13, further comprising means for breaking said seal.

15. An apparatus as claimed in claim 13 further comprising means for assaying the assay component of the fluid.

16. A device as claimed in claim 1 wherein the channel is slanted with respect to the longitudinal axis of the hub so that flow of fluid through the separation zone in the second and third configurations is facilitated by gravity.

17. A method for fluid assay comprising the steps of:
(a) contacting, in the device of claim 1, a body fluid to be assayed in the first chamber with assaying reagent in the first configuration;
(b) rotating the carousel to the second configuration;
(c) collecting a component to be assayed in at least one other chamber; and
(d) assaying the component.

* * * * *